United States Patent
Frigg

(10) Patent No.: US 10,463,359 B2
(45) Date of Patent: *Nov. 5, 2019

(54) DEVICE FOR ANCHORING A SUTURE

(71) Applicant: DePuy Synthes Products, Inc., Raynham, MA (US)

(72) Inventor: Robert Frigg, Langendorf (CH)

(73) Assignee: DePuy Synthes Product, Inc., Raynham, MA (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/693,101

(22) Filed: Aug. 31, 2017

(65) Prior Publication Data

US 2017/0360429 A1  Dec. 21, 2017

Related U.S. Application Data

(63) Continuation of application No. 13/221,577, filed on Aug. 30, 2011, now Pat. No. 9,775,596.

(60) Provisional application No. 61/383,984, filed on Sep. 17, 2010.

(51) Int. Cl.
  *A61B 17/04* (2006.01)
  *A61B 17/00* (2006.01)

(52) U.S. Cl.
  CPC ..... *A61B 17/0401* (2013.01); *A61B 2017/00862* (2013.01); *A61B 2017/042* (2013.01); *A61B 2017/0403* (2013.01); *A61B 2017/0409* (2013.01); *A61B 2017/0411* (2013.01); *A61B 2017/0414* (2013.01)

(58) Field of Classification Search
  CPC .................................................. A61B 17/0401
  See application file for complete search history.

(56) References Cited

U.S. PATENT DOCUMENTS

| | | |
|---|---|---|
| 881,819 A | 3/1908 | McIntosh |
| 5,207,679 A | 5/1993 | Li |
| 5,618,314 A | 4/1997 | Harwin et al. |
| 5,662,658 A | 9/1997 | Wenstrom, Jr. |
| 5,824,011 A | 10/1998 | Stone et al. |
| 6,048,309 A | 4/2000 | Flom et al. |
| 6,328,758 B1 | 12/2001 | Tornier et al. |
| 2002/0188305 A1 | 12/2002 | Foerster et al. |
| 2007/0032792 A1 | 2/2007 | Collin et al. |
| 2009/0248069 A1 | 10/2009 | Paulos |
| 2010/0211071 A1 | 8/2010 | Lettmann et al. |
| 2011/0022098 A1 | 1/2011 | Gilete Garcia |

FOREIGN PATENT DOCUMENTS

| | | |
|---|---|---|
| EP | 2 277 457 | 1/2011 |
| GB | 2312376 | 10/1997 |
| WO | 2008/109566 | 9/2008 |
| WO | 2008/109872 | 9/2008 |

*Primary Examiner* — Si Ming Ku
(74) *Attorney, Agent, or Firm* — Fay Kaplun & Marcin, LLP

(57) ABSTRACT

A device is for anchoring a suture to a bone. The device includes a suture engaged with an elastically deformable ring biased toward an unstressed state in which an outer diameter of the ring is D. The ring is compressible for insertion through a hole in a bone stabilization device having a diameter smaller than the diameter D.

20 Claims, 6 Drawing Sheets

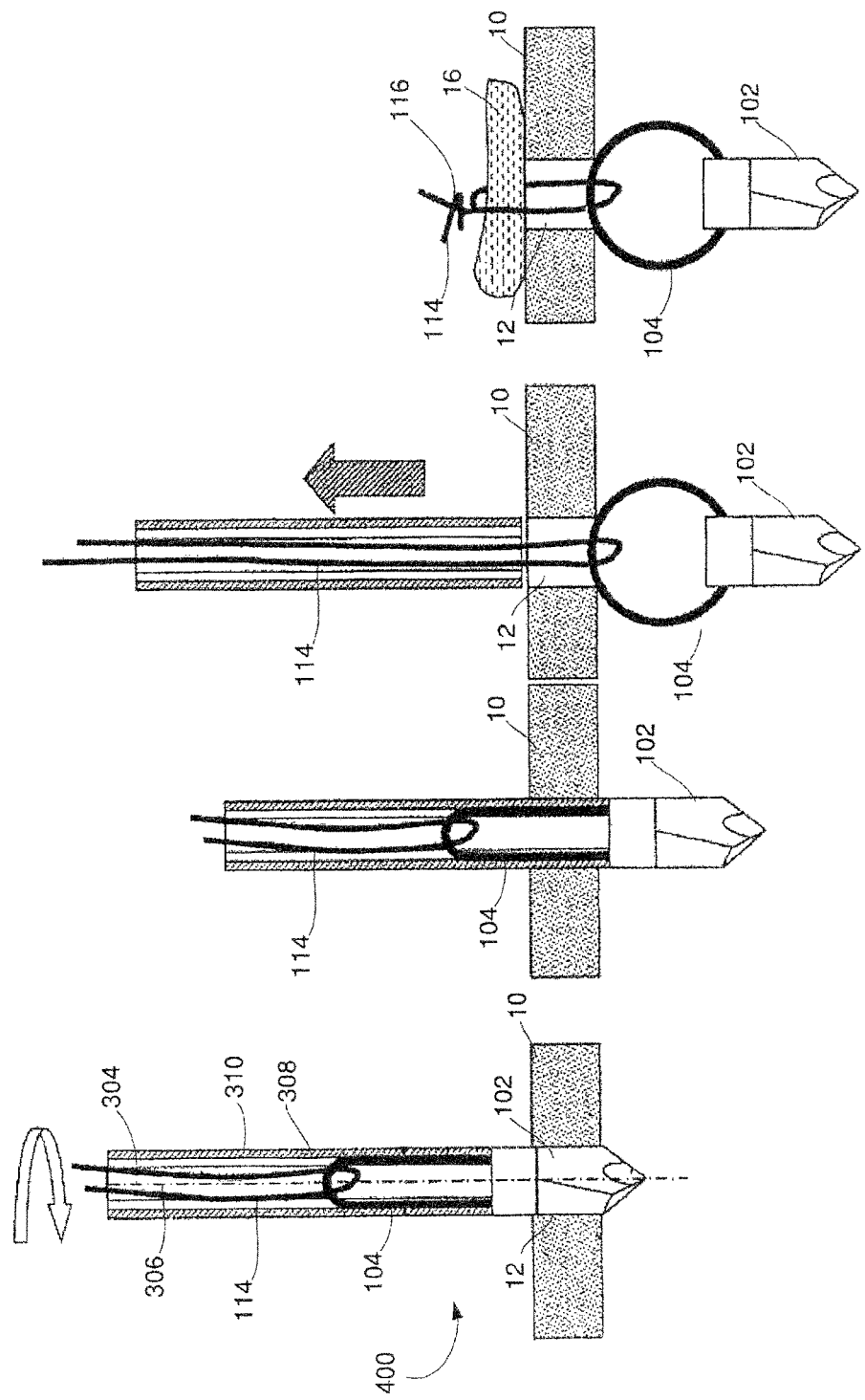

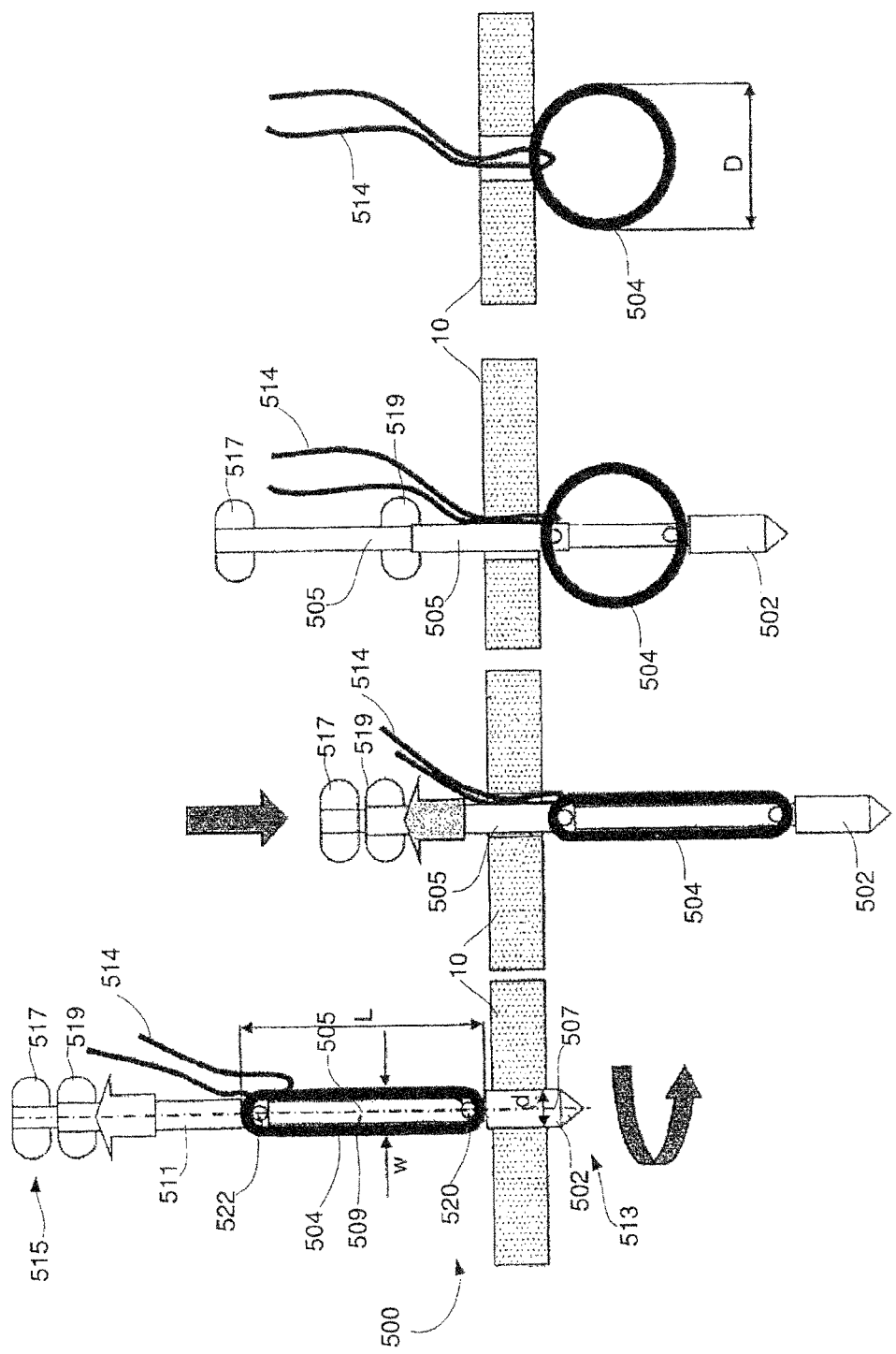

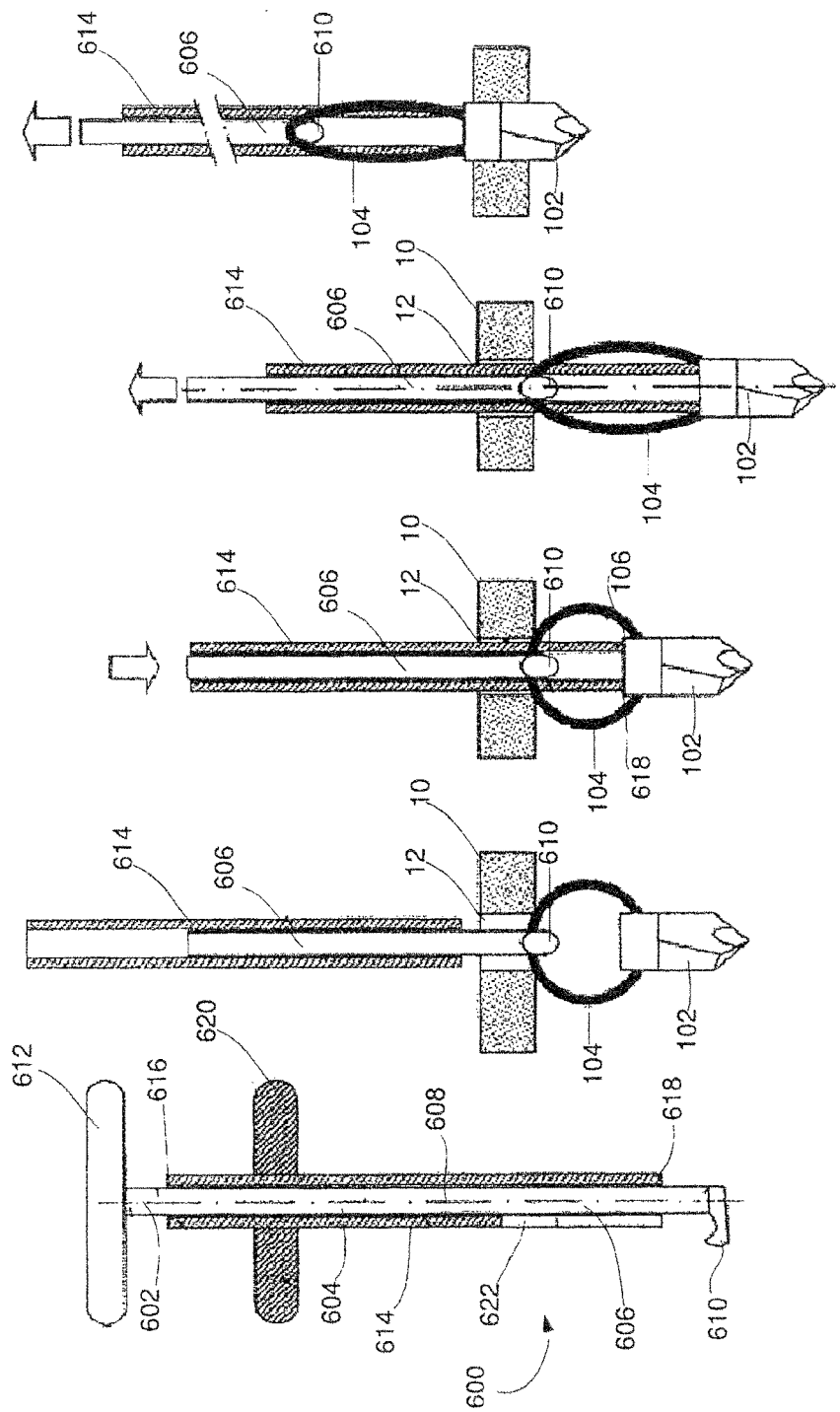

DEVICE FOR ANCHORING A SUTURE

PRIORITY CLAIM

The present application is a Continuation Application of U.S. patent application Ser. No. 13/221,577 filed on Aug. 30, 2011, now U.S. Pat. No. 9,775,596 issued Oct. 3, 2017; which claims priority to U.S. Provisional Application Ser. No. 61/383,984 filed on Sep. 17, 2010. The disclosures of the above patent(s)/applications are incorporated herein by reference.

FIELD OF THE INVENTION

The present invention generally relates to a device for anchoring a suture. More particularly, the present invention relates to a device for anchoring a suture in a living body, particularly in a bone of a patient. Exemplary embodiments of the present invention further relate to a kit including the device for anchoring the suture and a driver sleeve. The present invention also relates to a method for anchoring the suture in a body portion, particularly in a bone.

BACKGROUND

Conventional procedures for the fixation of bones often require predrilling of a bore hole in a target portion of bone using a drill bit often in conjunction with a drilling sleeve. Such procedures require the insertion and subsequent removal of the drill bit from the bone to permit the insertion of a bone fixation element (e.g., bone screw). These actions are often associated with physician errors. For example, a bone fixation element may inadvertently be inserted at an angle relative to a longitudinal axis of a bore drilled into the bone, decreasing a holding strength of the implanted fixation element, as those skilled in the art will understand.

SUMMARY OF THE INVENTION

The present invention relates to a device for anchoring a suture in a body portion, particularly in a bone of a patient with an anchoring element that can be directly and easily placed into a bone.

The present invention also relates to a device for anchoring a suture in a body portion, particularly in a bone of a patient comprising a suture and an elastically deformable ring having an outer diameter D. Suitably, the device has a drill bit coupled to the ring.

A substantially circular shape of the ring according to the invention prevents the ring from tilting during insertion thereof into a bore hole in the bone.

Surgical applications of the device according to the invention include, but are not limited to, fixation of a suture to a bone to permit an attachment of muscles and/or tendons to the bone; fixation of distal biceps tendons; and Anterior Cruciate Ligament/Posterior Cruciate Ligament fixation procedures.

In one exemplary embodiment of the device, the drill bit is coupled to the ring in a rotatably stable manner with regard to a central axis of the drill bit.

In a further exemplary embodiment of the device, the ring is laterally compressible to a smallest width W, wherein a ratio W/D is at least approximately 0.25 and preferably at least 0.3.

In another exemplary embodiment of the device, the ring is formed of one or more of titanium, a titanium alloy, an elastomer, and an amorphous glass metal. Glass metals can sustain larger reversible deformations than crystalline alloys of similar chemical composition.

In another exemplary embodiment of the device, the drill bit has a diameter d<D.

In yet another exemplary embodiment of the device, the minimum width W of the ring in a compressed state is smaller than or equal to the diameter d of the drill bit. The configuration offers the advantage that the compressed ring can pass through the bore hole which has been drilled by the drill bit.

In still another exemplary embodiment of the device, the drill bit comprises a transverse through opening for receiving a suture. In this exemplary embodiment, the suture can be tightened in such a way that a tensile force acting on strands thereof applies a compressive force on the ring arranged between the drill bit and the bone.

In a further exemplary embodiment of the device, the drill bit comprises a transverse through hole configured to receive an arc of the ring therethrough.

In again a further exemplary embodiment of the device, first and second recesses are arranged at diametrically opposed openings of the through hole, the first and second recesses being configured to receive a portion of the ring when said ring is in a compressed configuration. The ring can thus be compressed transversely to a central axis of said drill bit to the width W which is smaller than or equal to the diameter d of the drill bit.

A kit according to a further exemplary embodiment of the invention comprises the ring and a driver sleeve. The driver sleeve has a longitudinal axis, a central channel defining a peripheral inner wall and two first longitudinal grooves extending into the peripheral inner wall from the central channel, the first grooves being configured and dimensioned to receive diametrically opposed portions of the ring when the ring is in a compressed state. Suitably, the kit comprises the drill bit.

In another exemplary embodiment of the invention, the driver sleeve has an outer diameter which is smaller than or equal to the diameter d of the drill bit. This configuration offers the advantage that the driver sleeve can pass through the hole in the bone drilled by the drill bit.

In a further exemplary embodiment of the invention, the kit further comprises a removal instrument including an elongated rod having a rod axis and a hook at a distal end thereof, the hook being configured to engage a proximal portion of the ring. The kit further comprises a counterpressure tube disposed over the rod and being longitudinally displaceable relative thereto, the tube further comprising a slot extending proximally from a distal end thereof and being configured to receive the hook therethrough when the rod is moved proximally within the tube. The removal instrument is configured to elastically deform the ring. In this deformed state, the ring can be pulled through a hole in a bone.

In accordance with another exemplary embodiment of the invention, an assembly is provided for anchoring a suture in a body portion, particularly in a bone of a patient, the assembly comprising an anchoring means and an insertion instrument allowing the placement of the anchoring means within the bone. Suitably, where the device comprises a drill bit, the anchoring may be undertaken without the need of pre-drilling a hole thereinto.

According to a further exemplary embodiment of the invention, a method for anchoring a suture in a body portion, particularly in a bone of a patient using the kit according to the invention is provided. This method comprises the steps of: inserting an elastically deformable ring into a driver sleeve, the ring having an outer diameter D and being biased to a substantially circular shape, the driver having a longitudinal axis, a central channel defining a peripheral inner wall and two first longitudinal grooves extending into the inner peripheral wall from the central channel, the first longitudinal grooves being dimensioned to receive diametrically opposed portions of the ring in a compressed state; positioning a drill tip on a target surface of a body portion; drilling a hole into the target surface; pushing the driver sleeve into the target surface until the ring has reached a target depth past the target surface; retracting the driver sleeve proximally away from the ring so that the ring remains implanted at the target depth within the bone; and suturing a target body portion to the ring.

In another exemplary embodiment, where the drill tip is configured to receive a portion of the ring therethrough, the step of drilling comprises drilling the hole into the target surface by rotating the driver sleeve about its longitudinal axis. The driver sleeve may also be retracted proximally away from the drill tip and the drill tip may remain implanted within the bone.

In another exemplary embodiment, the method further comprises the step of: inserting the ring into the two first grooves.

According to a further exemplary embodiment of the invention, a method for anchoring a suture in a body portion, particularly in a bone of a patient using the assembly according to the invention is provided. The method comprises the following steps: coupling an elastically deformable ring having an outer diameter D and a substantially circular biased shape to a telescoping insertion instrument, the telescoping insertion instrument having a body extending from a proximal end to a distal end having a drill tip and comprising a coupling mechanism for coupling the ring thereto so that the ring is positioned along a longitudinal length of the insertion instrument; deforming the ring to an elongated configuration by moving first and second portions of the coupling mechanism telescopically away from one another; positioning the drill tip on a surface of a target body portion; drilling a hole into the target body portion by rotating the insertion instrument about a longitudinal axis thereof; inserting the insertion instrument into the hole until the ring reaches a target depth within the target body portion; decoupling the ring from the insertion instrument; removing the insertion instrument from the target body portion; and suturing a target body portion to the ring and drill tip.

BRIEF DESCRIPTION OF THE DRAWINGS

Several embodiments of the invention will be described in the following by way of example and with reference to the accompanying drawings in which:

FIG. 9 illustrates a first lateral view of a first exemplary method according to the invention;

FIG. 10 illustrates a second lateral view of a first exemplary method according to the invention;

FIG. 11 illustrates a third lateral view of a first exemplary method according to the invention;

FIG. 12 illustrates a fourth lateral view of a first exemplary method according to the invention;

FIG. 13 illustrates a first lateral view of a second exemplary method according to the invention;

FIG. 14 illustrates a second lateral view of a second exemplary method according to the invention;

FIG. 15 illustrates a third lateral view of a second exemplary method according to the invention;

FIG. 16 illustrates a fourth lateral view of a second exemplary method according to the invention;

FIG. 17 illustrates a first lateral view of a third exemplary method according to the invention;

FIG. 18 illustrates a second lateral view of a third exemplary method according to the invention;

FIG. 19 illustrates a third lateral view of a third exemplary method according to the invention;

FIG. 20 illustrates a fourth lateral view of a third exemplary method according to the invention; and FIG. 21 illustrates a fifth lateral view of a third exemplary method according to the invention.

DETAILED DESCRIPTION OF THE INVENTION

The present invention relates to a system and method for bone fixation comprising a bone drilling tip having an elongated body configured for drilling a borehole in a target portion of bone. A proximal portion of the bone drilling tip comprises a first transverse opening configured to receive a stabilization ring therethrough. The stabilization ring according to the present invention is biased to a substantially circular configuration and is formed of an elastic material permitting compression thereof as needed to permit insertion of the ring into the bone, as will be described in greater detail later on. A proximal portion of the stabilization ring according to the invention is configured to receive a suture which extends out of the bone when the drill bit is implanted to a target depth therein to permit a physician or other user to apply stress to the stabilization ring to manipulate a cross-sectional shape thereof within the bone while also permitting the physician to secure the stabilization ring and drilling tip to a muscle, tendon or other tissue adjacent an outer surface of the bone. It is noted that although the present invention has been described with respect to predetermined bone fixation procedures performed at predetermined depths in target bones, other bone fixation procedures may employ the apparatus of the invention without deviating from the scope of the present invention. As used herein, the term proximal refers to a direction approaching a physician or other user of the device while the term distal refers to a direction approaching a target treatment area within a patient.

Figure 2:
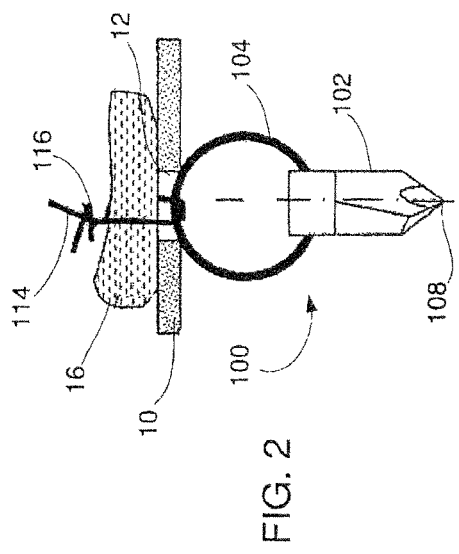
FIG. 2 illustrates a second lateral view of the device of FIG. 1 after insertion into a body.
Figure 3:
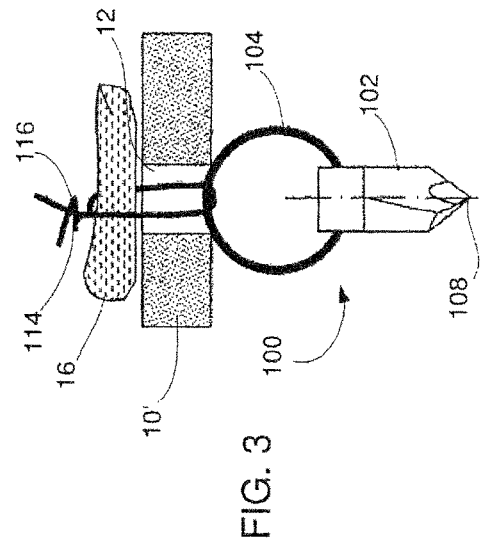
FIG. 3 illustrates a third lateral view of the device of FIG. 1 after insertion into a body.
Figure 1:
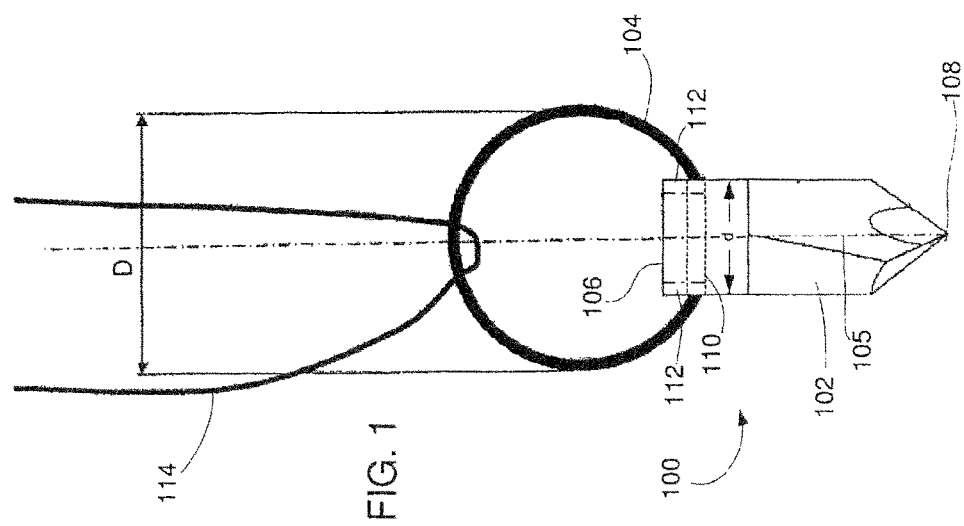
FIG. 1 illustrates a first lateral view of a first exemplary embodiment of the device according to the present invention.
Figure 7:
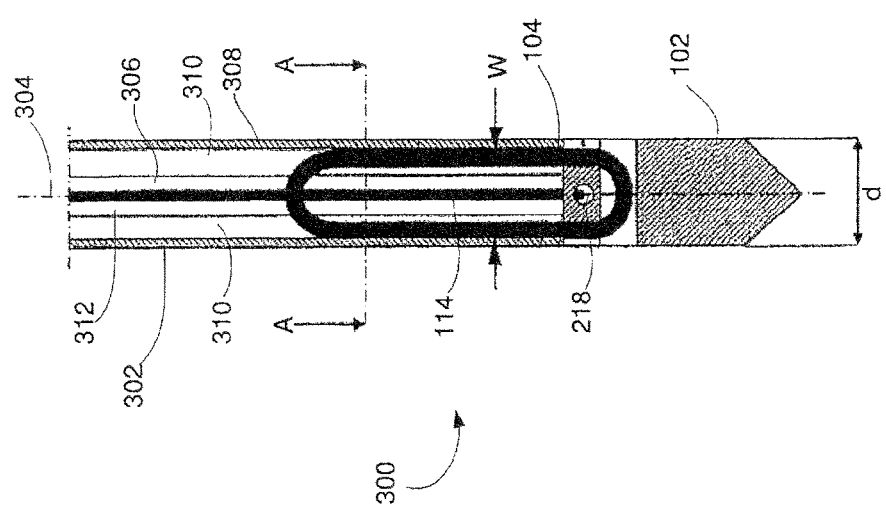
FIG. 7 illustrates a partial longitudinal cross-section of a kit according to another embodiment of the present invention.

As shown in FIGS. 1-3, a device 100 according to a first exemplary embodiment of the invention comprises a drill bit 102 configured to engage a deformable ring 104 having an outer diameter D. In an exemplary embodiment, the ring 104 is formed of titanium, a titanium alloy, an elastomer, a glass (e.g., an amorphous glass) and a metal or any combination of these materials. The drill bit 102 is an elongated substantially cylindrical element extending between a proximal end 106 and a sharpened distal tip 108 along a central longitudinal axis 105. A proximal region of the drill bit 102 comprises a transverse opening 110 (shown in phantom in FIG. 1) extending therethrough substantially perpendicular to the central longitudinal axis 105. The transverse opening 110 is configured and dimensioned to receive an arc of the elastically deformable ring 104. The transverse opening 110 further comprises recesses 112 at opposite ends thereof extending from the ends of the recesses 112 to the proximal end 106, each of the recesses 112 being sized to receive a portion of the ring 104 when the ring 104 is compressed against the drill bit 102 transversely to the central longitudinal axis 105, as will be described in greater detail later on. The recesses 112 are both open to the transverse opening 110 and extend proximally therefrom substantially parallel to the central longitudinal axis 105 of the drill bit 102. Furthermore, the recesses 112 are open to the proximal end 106 of the drill bit 107. The drill bit 102 has a diameter d less than the diameter D of the ring 104 so that, when inserted into the opening 110, a shape of a portion of the ring 104 extending outside the drill bit 102 is not substantially altered from its shape when unstressed. When constrained within a drill sleeve as will be discussed in more detail below, the ring 104 is compressed transversely to the central longitudinal axis 105 into the recesses 112 to a width W smaller than or equal to the diameter d of the drill bit 102, as illustrated in FIG. 7. A portion of the ring 104 passes through the transverse opening 110 to couple the ring 104 to the drill bit 102 in a rotatably stable manner with respect to the central longitudinal axis 105. The device 100 further comprises a suture 114 which may be looped over the ring 104 prior to insertion of the device 100 into a body, as will be described in greater detail hereinafter.

As shown in FIG. 2, the drill bit 102 is used to drill a hole 12 into a cortex of a bone 10. Thus the hole 12 has substantially the same diameter d as the drill bit 102. The drill bit 102 is advanced into spongy tissue (not shown) of the bone 10 until the entire ring 104 has been drawn through the cancellous bone into a cavity in the spongy tissue. At this point, the ring 104 returns to its unstressed state, expanding to its full diameter D. As the diameter D of the ring 104 is significantly greater than the diameter of the hole 12 in the bone 10, the ring 104 rigidly fixes the suture 114 to the bone 8 while strands thereof extend out of the bone 10 so that they are available for manipulation into a knot 116. For example, a knot 116 may be formed in the suture 114 around a ligament or tendon 16 to fix the ligament or tendon 16 to the bone 10. The exemplary system and method of the present invention permits the fixation of a ligament, tendon 16 or any other tissue to a bone 10 regardless of a position thereof within the body or the type of bone being treated. For example, as shown in FIG. 3, a bone 10' having a cortical region with a greater thickness than that of the bone 10 may be treated in substantially the same manner as described above with accommodations being made in the length of the suture 114, as those skilled in the art will understand.

Figure 6:
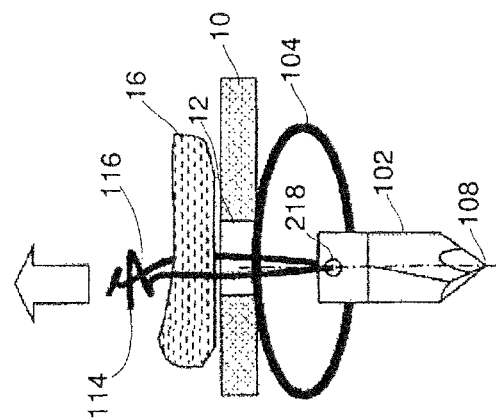
FIG. 6 illustrates a third lateral view of the device of FIG. 4 after insertion into a body.
Figure 5:
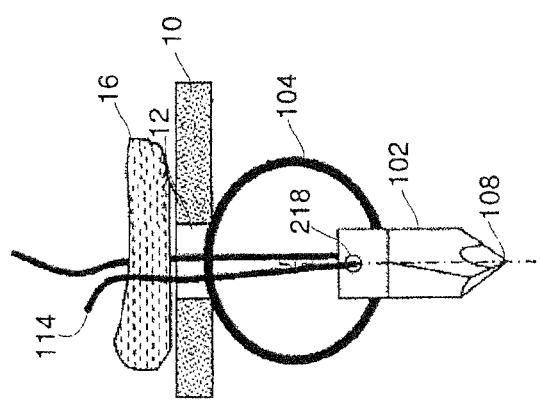
FIG. 5 illustrates a second lateral view of the device of FIG. 4 after insertion into a body.
Figure 4:
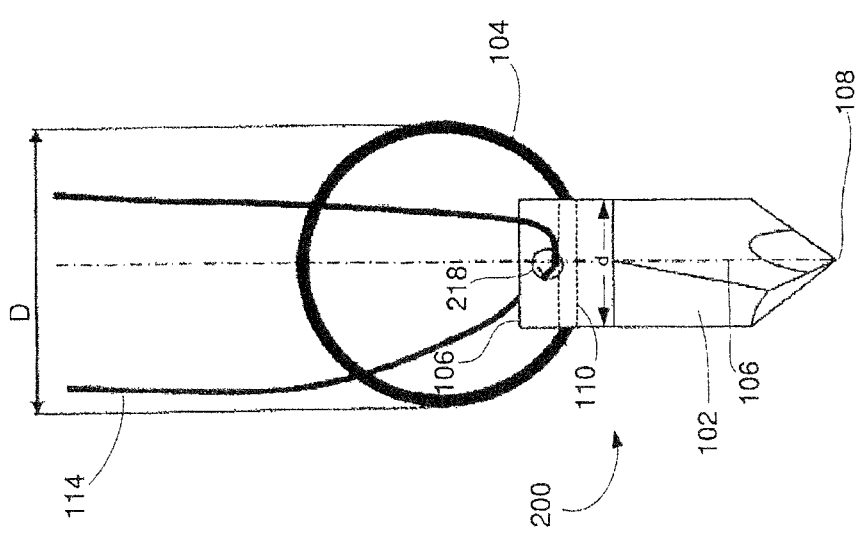
FIG. 4 illustrates a first lateral view of a second exemplary embodiment of the device according to the invention.

As shown in FIGS. 4-6, a device 200 according to a first alternate embodiment of the invention, is substantially similar to the device 100 with like elements being referenced with the same reference numerals. The device 200 differs from the device 100 in that an additional through opening 218 is provided between the transverse opening 110 and proximal end 106 of the drill bit 102. The through opening 218 extends substantially orthogonally to the central axis 105 of the drill bit 102 and transverse to the transverse opening 110 so that the suture 114 passing through the through opening 218 does not interfere with the ring 104. A loop of the suture 114 is passed through the through opening 218 prior to the insertion of the device 200 into a body opening or cavity, with first and second free ends (not shown) of the suture 114 being positioned laterally outside the ring 104. The device 200 is operated in substantially the same manner discussed above with respect to the device of FIGS. 1-3, wherein the hole 12 is drilled into the cortex of the bone 10 using the drill bit 102 coupled to a drill sleeve (not shown) so that the hole 12 has substantially the same diameter d. The drill sleeve is then withdrawn allowing the ring 104 to expand within the cavity in the spongy tissue of the bone 10 as shown in FIG. 5. As the diameter D of the ring 104 is significantly greater than the diameter d of the hole 12 in the bone 10, the ring 104 rigidly fixes the suture 114 to the bone 10 with the strands of the suture 114 extending from the loop through the drill bit 102 pass laterally on each side of the ring 104 out of the hole 12 in the bone 10 so that free ends thereof are accessible for forming a knot 116 to fix a ligament or tendon 16 to the bone 10. Furthermore, as shown in FIG. 6, the ring 104 can be elastically compressed in the direction of said central axis 105 of the drill bit 102 by tightening the knot 116 so that the ring 104 maintains a sufficient tensile force on the suture 114 preventing the knot 116 from loosening. That is, the tensile force longitudinally compresses the ring 104 to a substantially oval shape within the spongy tissue of the bone 10, drawing the drill bit 102 slightly proximally.

Figure 8:
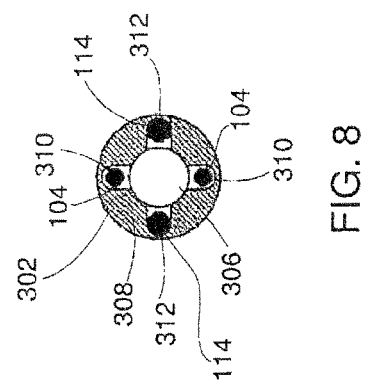
FIG. 8 illustrates a lateral cross section of the kit of FIG. 7.

As shown in FIGS. 7 and 8, a kit 300 according to another embodiment of the invention, comprises the device 200 FIGS. 4-6 and a driver sleeve 302 which is coupled to the proximal end 106 of the drill bit 102 to transmit driving torque to the drill bit 102 so that the hole 12 may be drilled in the bone 10. The driver sleeve 302 extends along a longitudinal axis 304 and includes a central channel 306 surrounded by a hollow cylindrical peripheral wall 308. An outer diameter of the driver sleeve 302 is substantially the same as the diameter d of the drill bit 102 so that the driver sleeve 302 can pass through the hole 12 in the bone 10. The driver sleeve 302 further comprises a first pair of diametrically opposed grooves 310 extending into the peripheral wall 308 from the channel 306, the first grooves 310 extending substantially coaxially to the longitudinal axis 304 of the driver sleeve 302. The first grooves 310 are configured and dimensioned to receive diametrically opposed portions of the ring 104 when the ring 104 is received therein in the laterally compressed state depicted in FIG. 7. The driver sleeve 302 further comprises a second pair of diametrically opposed grooves 312 extending into the peripheral wall 308 from the channel 306, the second grooves 312 being arranged substantially perpendicularly to the first grooves 310 when viewed in a cross-section of the driver sleeve 302 orthogonal to its longitudinal axis 304, as shown in FIG. 8. The second grooves 312 are configured and dimensioned to receive the strands of the suture 114 inserted through the through opening 218 of the drill bit 102. Thus, the suture 114 may pass through the central channel 306 without interfering with the portions of the compressed ring 104 inserted into the first grooves 310.

In accordance with an exemplary method for the kit 300, the proximal end 106 of the drill bit 102 is drawn proximally until the proximal end 106 of the drill bit 102 abuts the distal end of the driver sleeve 302 with the ring 104 compressed into the central channel 306 and received in the first grooves 310. The strands of the suture 114 are passed through the driver sleeve 302 within the second grooves 312 to extend out of a proximal end of the driver sleeve 302 where they are accessible to a user of the device. The drill bit 102 is then positioned over a target portion of bone and the driver sleeve 302. The first grooves 310 guide the ring 104 through the channel 306 so that the ring 104 remains substantially longitudinally aligned with the longitudinal axis 304 of the driver sleeve 302 during insertion. Similarly, the suture 114 is positioned to extend through the second grooves 312 of the driver sleeve 302 to prevent obstruction by the ring 104. Engagement of the ring 104 with the first grooves 310 transmits torque applied to the driver sleeve 302 to be to the ring 104 and, consequently to the drill bit 102 (via the portion of the ring 104 extending within the lateral opening 110). As those skilled in the art will understand, a proximal portion of the driver sleeve 302 may be connected to a drilling mechanism known in the art to apply the required torque. When the hole has been drilled through the cancellous bone and the drill bit 102 and ring 104 are within a cavity in the spongy bone, the driver sleeve 302 is withdrawn proximally over the suture 114 leaving the drill bit 102 and the ring 104 within the cavity in the spongy bone. As described above, the ring 104 reverts to its expanded configuration (with diameter D) when the constraint of the driver sleeve 302 is removed, locking the drill bit 102 within the bone 10. In a preferred embodiment, the driver sleeve 302 features a piston (not shown) arranged therewithin to ease the driver sleeve 302 proximally away from the bone without drawing the ring 104 and the drill bit 102 proximally out of the hole.

As shown in FIGS. 9-12, a kit 400 according to another embodiment of the invention includes the driver sleeve 302 in combination with the device 100 of FIGS. 1-3 instead of the device 200 of FIGS. 4-6. In this embodiment, the suture 114 attached to the ring 104 passes through the central channel 306 without interfering with any portion of the compressed ring 104 inserted into the first grooves 310. That is, in this embodiment, the suture 114 extends proximally from the ring 104 and therefore eliminates the need for second grooves 312 in the driver sleeve 302.

As shown in FIG. 9, after attaching a suture 114 to the ring 104, the ring 104 is compressed in a direction substantially orthogonal to the longitudinal axis 304 of the driver sleeve 302 to a width W and inserted into the central channel 306 of the driver sleeve 302 so that lateral portions of the ring 104 are positioned within the first grooves 310, as described in greater detail earlier and the drill bit 102 is drawn proximally until the proximal end 106 engages a distal end of the driver sleeve 302 (e.g., by withdrawing the suture 114 proximally out of the driver sleeve 302. As shown in FIG. 9-10, the drill tip 102 is then positioned on the surface of a body portion (e.g. on the surface of the bone 10 to which the suture 114 is to be affixed) and the hole 12 is drilled into the cortex of the bone 10 by rotating the driver sleeve 302 about its longitudinal axis 306. Rotation of the driver sleeve 302 may be carried out by a driving mechanism (not shown), as those skilled in the art will understand. The driver sleeve 302 with the ring 104 attached thereto is advanced through the hole 12 drilled by the drill bit 102 until the ring 104 is positioned distally of the cortical tissue of the bone 10, as shown in FIG. 10. Once the ring 104 is positioned within a cavity in the spongy tissue of the bone 10 or another target portion of the bone. The driver sleeve 302 is retracted proximally freeing the ring 104 from the constraint of the driver sleeve 3020 allowing the ring 104 to assume its substantially circular configuration, locking the ring 104 and the drill bit 102 within the bone 10 as shown in FIG. 11. The driver sleeve 302 is slid over the strands of the suture 114 until the suture 114 is withdrawn from the driver sleeve 302. As shown in FIG. 12, a knot 116 is then formed in the suture 114 and tightened over a ligament or tendon 16 to secure the ligament or tendon 16 at a desired position over the bone 10. It is further noted that, if deemed necessary by a physician or other user, any amount of torque may be applied to the suture 114 and, consequently to the ring 104, to longitudinally compress the ring 104 to maintain tension on the suture 114 as described above.

As shown in FIGS. 13 to 16, a device 500 according to another embodiment of the present invention includes an insertion instrument 505 facilitating insertion of a drill tip 502 having a diameter d into the bone 10. The device 500 comprises an elastically deformable ring 504 formed substantially similarly to the ring 104 and a suture 514 looped around the ring 504. The ring 504 is substantially circular with an outer diameter D in an undeformed state to which it is biased and is sufficiently elastic that it may be compressed to the elongated configuration shown in FIG. 13 for attachment to the insertion instrument 505.

The insertion instrument 505 includes a central rod body 509 extending along a longitudinal axis 507 and a sliding member 511 longitudinally displaceable relative to the central rod body 509. The central rod body 509 extends from a distal end 513 formed as a drill bit 502 having a diameter d to a proximal end 515 having a first handle 517. A proximal end of the sliding member 511 comprises a second handle 519 distal of the first handle 517.

The ring 504 is attached to the central rod body 509 by a first protrusion 520 extending transversely from the rod body 509 to engage an inner surface of the ring 504, as shown in FIG. 13. A second protrusion 522 extends transversely from a distal portion of the sliding member 511. The second protrusion 522 also extends transversely to the longitudinal axis 14 of the insertion instrument 505 and is positioned on the same side of the insertion instrument 505 as the first protrusion 522 to permit the ring 504 to be laterally coupled to the insertion instrument 505. As will be understood by those of skill in the art, the protrusions 520, 522 can be any shape suitable for holding the ring 504 on the insertion instrument 505 during insertion. For example, the protrusions 520, 522 may be hook or rod shaped.

To permit insertion of the ring 504 over the first and second protrusions 520, 522 the sliding member 511 is moved to a first axial position so that a distance L between the first and second protrusions 520, 522 is substantially equivalent to or smaller than the unstressed diameter D of the ring 504. Once the ring 504 has been so positioned, the sliding member 511 is moved proximally relative to the central rod body 509 to a second axial position in which first and second protrusions 520, 522 are separated by a distance L greater than the diameter D so that the ring 504 is longitudinally stretched and transversely compressed to a width W<d. Once the ring 504 has been positioned over the protrusions 520, 522 and moved to the second axial position shown in FIG. 13, it is held in position either manually by an operator or by a releasable locking mechanism (not shown) as would be understood by those of skill in the art. The drill tip 502 is then positioned on the surface of a body portion (e.g. on the target surface of a bone 10). The insertion instrument 505 is then rotated about its longitudinal axis 507 (e.g., via a connection (not shown) to a drilling mechanism) to drill the hole 12 into the cortical tissue of the bone 10 until the ring 504 is positioned within a cavity in the spongy tissue of the bone 10 as shown in FIG. 14. Once the ring 504 has reached a target position within the bone 10, the insertion instrument 505 is returned to the first axial position to remove the expansive force applied to the ring 504 so that the ring 504 returns to its unstressed circular configuration as shown in FIG. 15 anchoring the suture 514 within the bone 10. Specifically, the insertion instrument 505 is moved to the first axial position by applying a distally directed force to the second handle 519 while maintaining a position of the first handle 517. As would be understood by those of skill in the art, this force may be applied manually by an operator and/or may result from the force of the ring 504 returning to its unstressed state. The insertion instrument 505 may then be rotated to completely disengage the ring 504 from the first and second protrusions 520, 522 and the insertion instrument 505 is withdrawn proximally from the hole 12 formed in the bone 10. As shown in FIG. 16, removal of the insertion instrument 505 leaves only the ring 504 and the suture 514 within the bone 10. In a subsequent step (not shown), suturing may be performed in accordance with the methods described earlier.

As shown in FIGS. 17 to 21, an embodiment of a removal instrument 600 for removing a device 102 from the bone 10 includes a pulling member 602 and a counterpressure member 604. The pulling member 602 comprises a rod 606 extending along a rod axis 608 with a hook 610 at a distal end and a pulling handle 612 at its proximal end. The counterpressure member 604 includes a tube 614 slidably received over the rod 606 so that it is coaxially displaceable relative to the rod 35 along the rod axis 34. The tube 614 extends from a proximal end 616 to a distal end 618 and includes a pushing handle 620 arranged near the proximal end 616. The tube 614 further comprises a slot 622 coaxially extending from the distal end 618 by a length selected to permit a predetermined range of motion of the pulling member 302 relative to the counterpressure member 604. Specifically, the slot 622 is configured and dimensioned to receive the hook 610 therethrough when the pulling member 602 is coaxially displaced relative to the counterpressure member 604 toward the proximal end 616 of the tube 614. As illustrated in FIG. 18, in a first position, the ring 104 and drill bit 102 are implanted in a spongy layer of the bone 10. In a first operative configuration, the rod 606 is advanced through the hole 12 in the bone 10 until the hook 610 engages the ring 104. Once the hook 610 is attached to the ring 104, the tube 614 of the counterpressure member 604 is advanced through the hole 12 until its distal end 618 abuts the proximal end 106 of the drill bit 102, as shown in FIG. 19. As shown in FIG. 20, a proximally directed force is then applied to the pulling handle 612 to pull the rod 606 axially away from the drill bit 102 while maintaining a position of the pushing handle 620 and tube 614. This movement causes the ring 104 to be longitudinally deformed so as to be elongated along the rod axis 608 while being simultaneously contracted orthogonally to the rod axis 608. In this deformed state, a width of the ring 104 is substantially equivalent to or smaller than a diameter of the hole 12, thus permitting a proximal withdrawal of the ring 102 therefrom. Specifically, as shown in FIG. 21, once the ring 104 assumes an elongated configuration, the pulling handle 612 and pushing handle 620 are simultaneously moved proximally to apply the proximally directed force to the ring 104 and drill bit 102 to withdraw these elements from the bone 10.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A kit for anchoring a suture to a bone, comprising:
a suture;
an elastically deformable ring biased toward an unstressed state in which the ring has an outer diameter of D, the ring being compressible for insertion through a hole in a bone stabilization device having a diameter smaller than the outer diameter (D) of the ring; and
a driver sleeve extending along a first longitudinal axis and including a central channel, a peripheral inner wall and two first longitudinal grooves extending into the peripheral inner wall from the central channel, the first longitudinal grooves being dimensioned to receive opposed portions of the ring in an elongated state.

2. The kit according to claim 1, wherein the ring is compressible into an elongated shape having a width W.

3. The kit according to claim 1, further comprising:
a drill bit extending from a proximal end to a distal end and having a second longitudinal axis extending therebetween, the drill bit being configured to receive a portion of the ring therethrough, the drill bit having a diameter d<D, wherein the ring is formed of a material sufficiently elastic that the ring may be moved to a compressed state in which a width W of the ring is no greater than d.

4. The kit according to claim 3, wherein an outer diameter of the driver sleeve is no greater than a diameter d of the drill bit.

5. The kit according to claim 3, wherein the width W of the ring in the elongated shape is measured orthogonally to the longitudinal axis of the drill bit.

6. The kit according to claim 3, wherein the drill bit comprises a transverse through opening sized to receive a suture therein.

7. The kit according to claim 1, further comprising:
a removal instrument including an elongated rod having a rod axis and a hook at a distal end thereof configured to engage a proximal portion of the ring and a counterpressure tube slidably disposed over the rod, the tube further comprising a slot extending proximally from a distal end thereof and being configured to slidably receive the hook therethrough when the rod is moved proximally within the tube.

8. The kit according to claim 7, wherein a proximal end of the rod comprises a first handle and a proximal end of the tube comprises a second handle.

9. The kit according to claim 7, wherein the hook extends out of the rod substantially perpendicular to the rod axis.

10. The kit according to claim 1, wherein the driver sleeve further comprises two second grooves extending into the peripheral inner wall from the central channel, the second longitudinal grooves being dimensioned to receive diametrically opposed portions of the suture attached to one of the ring and the drill bit.

11. The kit according to claim 10, wherein the two second grooves are offset from the two first grooves about a circumference of the driver sleeve so that the suture does not interfere with the ring.

12. The kit according to claim 1, wherein the ring is formed of one of titanium, a titanium allow, an elastomer and a glass metal.

13. A kit for anchoring a suture to a bone, comprising:
a suture;
an elastically deformable ring biased toward an unstressed state in which the ring has an outer diameter of D, the ring being compressible for insertion through a hole in a bone stabilization device having a diameter smaller than the outer diameter (D) of the ring;
a drill bit extending along a longitudinal axis from a boring distal point to a proximal portion coupled to the ring; and
a driver sleeve extending along a first longitudinal axis and including a central channel, a peripheral inner wall and two first longitudinal grooves extending into the peripheral inner wall from the central channel, the first longitudinal grooves being dimensioned to receive opposed portions of the ring in an elongated state.

14. The kit according to claim 13, wherein the ring is compressible into an elongated shape having a width W.

15. The kit according to claim 13, wherein a diameter of the drill bit is smaller than the outer diameter D of the ring in the unstressed state.

16. The kit according to claim 13, wherein an outer diameter of the driver sleeve is no greater than a diameter d of the drill bit.

17. The kit according to claim 13, further comprising:
a removal instrument including an elongated rod having a rod axis and a hook at a distal end thereof configured to engage a proximal portion of the ring and a counterpressure tube slidably disposed over the rod, the tube further comprising a slot extending proximally from a distal end thereof and being configured to slidably receive the hook therethrough when the rod is moved proximally within the tube.

18. The kit according to claim 17, wherein a proximal end of the rod comprises a first handle and a proximal end of the tube comprises a second handle.

19. The kit according to claim 17, wherein the hook extends out of the rod substantially perpendicular to the rod axis.

20. The kit according to claim 13, wherein the driver sleeve further comprises two second grooves extending into the peripheral inner wall from the central channel, the second longitudinal grooves being dimensioned to receive diametrically opposed portions of the suture attached to one of the ring and the drill bit.

* * * * *